US009802923B2

(12) United States Patent
Kumar et al.

(10) Patent No.: US 9,802,923 B2
(45) Date of Patent: Oct. 31, 2017

(54) PROCESS FOR THE PREPARATION OF PAZOPANIB OR SALTS THEREOF

(71) Applicant: RANBAXY LABORATORIES LIMITED, New Delhi, Delhi (IN)

(72) Inventors: Rajesh Kumar, Unnao (IN); Prabhat Giri, New Delhi (IN); Dhiren C. Barman, Gurgaon (IN); Asok Nath, Gurgaon (IN); Mohan Prasad, Haryana (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 84 days.

(21) Appl. No.: 14/652,807

(22) PCT Filed: Dec. 17, 2013

(86) PCT No.: PCT/IB2013/061048
§ 371 (c)(1),
(2) Date: Jun. 17, 2015

(87) PCT Pub. No.: WO2014/097152
PCT Pub. Date: Jun. 26, 2014

(65) Prior Publication Data
US 2015/0329526 A1    Nov. 19, 2015

(30) Foreign Application Priority Data
Dec. 17, 2012    (IN) ............................ 3897/DEL/2012

(51) Int. Cl.
*C07D 403/12*    (2006.01)

(52) U.S. Cl.
CPC .................................. *C07D 403/12* (2013.01)

(58) Field of Classification Search
CPC ...................................................... C07D 403/12
See application file for complete search history.

(56) References Cited

U.S. PATENT DOCUMENTS 7,105,530 B2 *    9/2006    Boloor ................. C07D 231/56
514/275

FOREIGN PATENT DOCUMENTS

| WO | WO 03/106416 | 12/2003 | ........... C07D 239/84 |
| WO | WO 2005/054212 | 6/2005 | ........... C07D 249/22 |
| WO | WO 2007/064752 | 6/2007 | ........... A61K 31/506 |
| WO | WO 2011/069053 | 6/2011 | ........... C07D 403/12 |
| WO | WO 2012/051659 | 4/2012 | ........... C07D 231/56 |

OTHER PUBLICATIONS

Reduction-of-Nitro, 2015, https://en.wikipedia.org/wiki/Reduction_of_nitro_compounds.*
Davies, "Indazole Derivatives: The Synthesis of Various Amino- and Hydroxy-indazoles and Derived Sulphonic Acids," *Journal of the Chemical Society*, pp. 2412-2423 (1955).

* cited by examiner

*Primary Examiner* — Sun Jae Yoo

(57) ABSTRACT

The present invention provides a process for the preparation of pazopanib of Formula Ia or salts, and intermediates thereof.

6 Claims, No Drawings

PROCESS FOR THE PREPARATION OF PAZOPANIB OR SALTS THEREOF

FIELD OF THE INVENTION

The present invention provides a process for the preparation of pazopanib of Formula Ia or salts, and intermediates thereof.

BACKGROUND OF THE INVENTION

Pazopanib is a tyrosine kinase inhibitor of Formula Ia.

Formula Ia

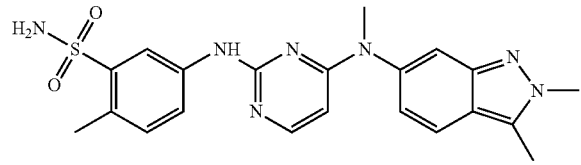

Pazopanib is marketed as the hydrochloride salt, with the chemical name 5-[[4-[(2,3-dimethyl-2H-indazol-6-yl)methylamino]-2-pyrimidinyl]amino]-2-methylbenzenesulfonamide monohydrochloride, having the structure as depicted in Formula I:

Formula I

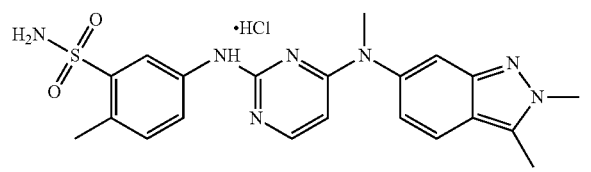

U.S. Pat. No. 7,105,530 provides a process for the preparation of a hydrochloride salt of a compound of Formula II Formula II

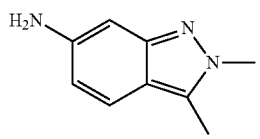

involving the reduction of 2,3-dimethyl-6-nitro-2H-indazole with tin (II) chloride in concentrated hydrochloric acid in the presence of 2-methoxyethyl ether at 0° C. It also describes the preparation of a compound of Formula III Formula III

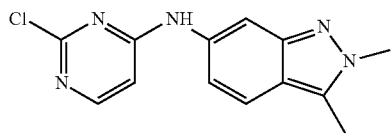

involving the reaction of a hydrochloride salt of compound of Formula II with 2,4-dichloropyrimidine in the presence of a base and solvent mixture of tetrahydrofuran/ethanol followed by stirring for 4 hours at 85° C.

PCT Publication No. WO 2007/064752 provides a process for the preparation of a compound of Formula II comprising reducing 2,3-dimethyl-6-nitro-2H-indazole with 10% Palladium-carbon (50% wet) in the presence of methanol, followed by the addition of ammonium formate at a rate that ensures the reaction temperature is maintained at or between 25° C. and 30° C. It also discloses the preparation of a compound of Formula III comprising heating the compound of Formula II with sodium bicarbonate in presence of tetrahydrofuran and ethanol at or between 75° C. and 80° C. followed by cooling to 20° C. to 25° C.

The present invention provides a process for the preparation of a compound of Formula II which offers recycling of the Raney nickel catalyst used in the process, and an easy filtration work-up procedure. Further, the present invention offers selective reduction under mild conditions that is economical to use at an industrial scale.

The present invention also provides a process for the preparation of compound of Formula III which avoids the use of two or more solvents, and additionally, also circumvents heating and cooling procedures during the reaction. The aforesaid advantages yield a compound of Formula III with a lesser amount of N-(4-chloropyrimidin-2-yl)-2,3-dimethyl-2H-indazol-6-amine (CPDMI) impurity.

The compounds of Formula II and Formula III prepared by the present invention yield a compound of Formula Ia or its salts in comparable yield and suitable purity required for medicinal preparations.

SUMMARY OF THE INVENTION

A first aspect of the present invention provides a process for the preparation of pazopanib of Formula Ia or its salts Formula Ia

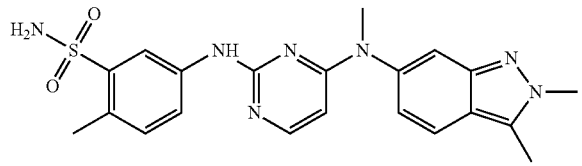

comprising:
i) treating 2,3-dimethyl-6-nitro-2H-indazole with Raney nickel to obtain a compound of Formula II;

Formula II

ii) treating the compound of Formula II at a temperature of about 45° C. or below with 2,4-dichloropyrimidine to obtain a compound of Formula III;

Formula III

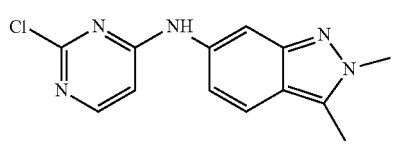

iii) converting the compound of Formula III to pazopanib of Formula Ia or its salts; and iv) isolating pazopanib of Formula Ia or its salts.

A second aspect of the present invention provides a process for the preparation of pazopanib of Formula Ia or its salts

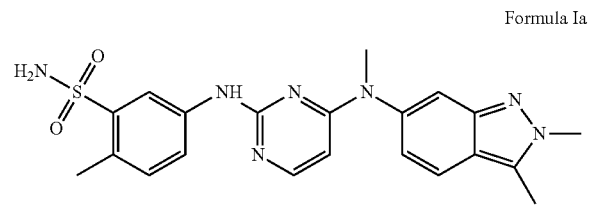 [SMILES: Cc1ccc(Nc2nccc(N(C)c3ccc4c(C)n(C)nc4c3)n2)cc1S(N)(=O)=O]

Formula Ia comprising:

i) treating 2,3-dimethyl-6-nitro-2H-indazole with Raney nickel to obtain a compound of Formula II;

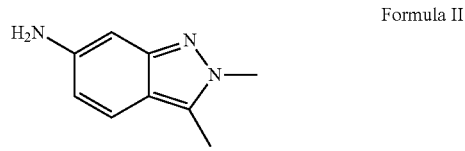

Formula II ii) treating the compound of Formula II with 2,4-dichloropyrimidine to obtain a compound of Formula III;

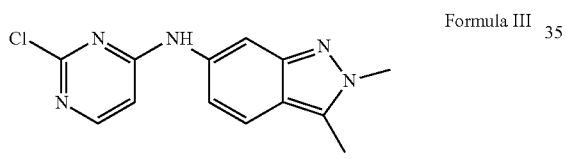

Formula III iii) converting the compound of Formula III to pazopanib of Formula Ia or its salts; and iv) isolating pazopanib of Formula Ia or its salts wherein the compound of Formula II is not isolated from the reaction mixture.

DETAILED DESCRIPTION OF THE INVENTION

Various embodiments and variants of the present invention are described hereinafter.

The term "about", as used herein, refers to ±5% variation in the values mentioned herein.

The 2,3-dimethyl-6-nitro-2H-indazole may be prepared by processes known in the prior art, for example, the process known in PCT Publication No. WO 2007/064752, or may be prepared by the process provided herein.

The Raney nickel used in the reaction is in the form of a fine grained solid. Step i) is carried out in the presence of an organic solvent and hydrogen gas. The organic solvent may be an alcoholic solvent. Examples of the alcoholic solvents include methanol, ethanol, n-propanol, iso-propanol, n-butanol, iso-butanol, sec-butanol, or mixtures thereof. The compound of Formula II may be isolated from the reaction mixture or may be carried as such on to step ii) without isolation. The compound of Formula II may be isolated from reaction mixture by any method known in the art. The catalyst Raney nickel is recovered back and recycled.

The compound of Formula II may be further treated with suitable solvents, or mixtures thereof The treatment of compound of Formula II with solvents may include preparing a suspension, stirring, or slurrying. Examples of the solvents to be used include halogenated solvents, aliphatic hydrocarbon solvents, or mixtures thereof Examples of halogenated solvents include dichloromethane, dichloroethane, chloroform, and carbon tetrachloride. Examples of aliphatic hydrocarbons include n-pentane, n-hexane, n-heptane, and n-octane.

Step ii) is carried out in the presence of an organic solvent and a base. Examples of organic solvents include alcoholic solvents like methanol, ethanol, n-propanol, iso-propanol, n-butanol, iso-butanol, sec-butanol, or mixtures thereof The base may be selected from organic or inorganic bases. The organic base is selected from the group comprising N,N-diisopropylethylamine, triethylamine, tri-isopropylamine, N,N-2-trimethyl-2-propanamine, N-methylmorpholine, 4-dimethylaminopyridine, 2,6-di-tert-butyl-4-dimethylaminopyridine, 1,4-diazabicyclo[2.2.2]octane, 1,8-diazabicyclo[5.4.0]undec-7-ene, or mixtures thereof. The inorganic base is selected from the group comprising sodium carbonate, potassium carbonate, sodium hydride, sodium bicarbonate, potassium bicarbonate, or mixtures thereof.

Step ii) is carried out at a temperature of about 45° C. or below, for example, at about 25° C. to 30° C. The temperature of about 45° C. or below is critical for controlling the formation of N-(4-chloropyrimidin-2-yl)-2,3-dimethyl-2H-indazol-6-amine impurity (4-CPDMI as disclosed in PCT Publication No. WO 2011/069053) during step ii).

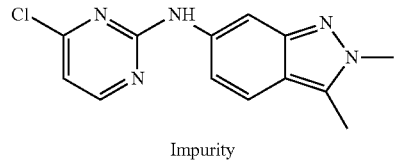 [SMILES: Cc1c2ccc(Nc3nccc(Cl)n3)cc2nn1C]

Impurity

The compound of Formula III is subjected to sequential treatment with water and an organic solvent. The treatment of the compound of Formula III with water and an organic solvent may include preparing a suspension, stirring, or slurrying. The organic solvent is selected from the group comprising ethyl acetate, n-propyl acetate, butyl acetate, or mixtures thereof The compound of Formula III may be isolated from the reaction mixture or may be carried as such on to step iii) without isolation. The compound of Formula III may be isolated from the reaction mixture by any method known in the art.

Step iii) may be carried out as per the embodiments described hereinafter, or by any other method known in the art.

The isolation of pazopanib or its salts is carried out by any method known in the art.

The salt of pazopanib is the hydrochloride salt of Formula I.

The compound of Formula I prepared by the process of the present invention may be further converted to pazopanib hydrochloride thereof by any method known to a person skilled in the art.

In the following section, preferred embodiments are described by way of examples to illustrate the process. However, these are not intended in any way to limit the

EXAMPLES

Step 1: Synthesis of 2,3-dimethyl-6-nitro-2H-indazole

Example 1

Trimethyloxonium tetrafluoroborate (125.2 g, 0.85 mol) was added to a stirred suspension of 3-methyl-6-nitro-indazole (100 g, 0.56 mol) in ethyl acetate (2000 mL) over a period of 4 hours in four equal lots at 1 hour time intervals. The reaction mixture was stirred at 25° C. to 30° C. for 16 hours. The solvent was recovered under reduced pressure. A saturated sodium bicarbonate solution (3240 mL) was added to the mixture slowly, and the reaction mixture was extracted with 4:1 mixture of dichloromethane isopropyl alcohol (1080 mL×5). The solvent was recovered under reduced pressure. Methyl tert-butyl ether (800 mL) was added to the residue, and the reaction mixture was stirred for 30 minutes at 45° C. to 50° C. The reaction mixture was cooled to 25° C. to 30° C. and was stirred at this temperature for 30 minutes. The solid was filtered, washed with methyl tert-butyl ether (100 mL×2), and dried in an air oven at 50° C. for 12 hours to afford 2,3-dimethyl-6-nitro-2H-indazole as a yellow solid.

Yield: 82.4% w/w

Step 2: Synthesis of 2,3-dimethyl-2H-indazol-6-amine

Example 2a

Raney nickel (12.50 g) was added to a suspension of 2,3-dimethyl-6-nitro-2H-indazole (50 g, 0.26 mol) in methanol (500 mL). The reaction mixture was stirred in an autoclave under hydrogen pressure of 3.5 kg/cm$^2$-4.0 kg/cm$^2$ at 25° C. to 30° C. for 5 hours. Further, the reaction mixture was filtered through a hyflo bed, and the catalyst was washed with methanol (100 mL×2). The filtrates were combined, and the solvent was recovered completely. n-Heptane (250 mL) and dichloromethane (50 mL) were added to the residue, and the reaction mixture was stirred for 1 hour at 25° C. to 30° C. The solid was collected by filtration, washed with n-heptane (50 mL×2), and dried under vacuum at 40° C. to 45° C. to afford 2,3-dimethyl-2H-indazol-6-amine as a light brown solid.

Yield: 95% w/w

Example 2b

Raney nickel (21.25 g) was added to a suspension of 2,3-dimethyl-6-nitro-2H-indazole (85 g, 0.45 mol) in methanol (850 mL). The reaction mixture was stirred in an autoclave under hydrogen pressure of 3.5 kg/cm$^2$-4.0 kg/cm$^2$ at 25° C. to 30° C. for 5 hours.

Further, the reaction mixture was filtered through a hyflo bed, and the catalyst was washed with methanol (85 mL×3). The filtrates were combined, and the solvent was recovered up to the volume of 850 mL. The 2,3-dimethyl-2H-indazol-6-amine in methanol was used as such in the next step.

Step 3: Synthesis of N-(2-chloropyrimidin-4-yl)-2,3-dimethyl-2H-indazol-6-amine

Example 3

Sodium bicarbonate (112 g, 1.34 mol) was added to a stirred solution of 2,3-dimethyl-2H-indazol-6-amine (as obtained from step 2; Examples 2a and 2b) in methanol 2,4-Dichloropyrimidine (99.35 g, 0.67 mol) was added to the reaction mixture followed by stirring of the reaction mixture for 24 hours at 25° C. to 30° C. De-ionized water (850 mL) was added to the reaction mixture followed by stirring of the reaction mixture at 25° C. to 30° C. for 1 hour. The solid was filtered. The wet solid was washed with de-ionized water (170 mL×2) to obtain a wet material. De-ionized water (850 mL) was added to the wet material to obtain a slurry, and the slurry was stirred at 25° C. to 30° C. for 30 minutes. The solid was filtered, then washed with de-ionized water (170 mL×2). The wet material obtained was treated with ethyl acetate (340 mL) to obtain a slurry. The slurry was stirred at 35° C. to 40° C. for 30 minutes and then cooled to 0° C. to 5° C. The slurry was further stirred at 0° C. to 5° C. for 30 minutes. The solid was collected by filtration, then washed with cold ethyl acetate (170 mL×2). The solid was dried in an air oven at 50° C. for 16 hours to afford N-(2-chloropyrimidin-4-yl)-2,3-dimethyl-2H-indazol-6-amine as an off-white solid.

Yield: 86.7% w/w

Step 4: Synthesis of Pazopanib Hydrochloride

Example 4a

Synthesis of N-(2-Chloropyrimidin-4-yl)-N,2,3-trimethyl-2H-indazol-6-amine

Cesium carbonate (238 g, 0.73 mol) and iodomethane (57 g, 0.40 mol) were added to a stirred suspension of N-(2-chloropyrimidin-4-yl)-2,3-dimethyl-2H-indazol-6-amine (100g, 0.37 mol) in N,N-dimethylformamide (300 mL) at 25° C. to 30° C. The reaction mixture was further stirred at 25° C. to 30° C. for 6 hours followed by cooling of the reaction mixture to 0° C. to 5° C. De-ionized water (300 mL) was added drop-wise to the reaction mixture, then the reaction mixture was stirred at 5° C. to 10° C. for 30 minutes. The solid was collected by filtration, and washed with de-ionized water (100 mL×2). The wet material so obtained was dried in an air oven at 50° C. for 12 hours to obtain the title compound.

Yield: 90.4% w/w

Example 4b

Synthesis of Pazopanib Hydrochloride

To a suspension of N-(2-chloropyrimidin-4-yl)-N-2,3-trimethyl-2H-indazol-6-amine (90 g, 0.312 mol) and 5-amino-2-methyl benzene sulfonamide (64.07 g, 0.344 mol) in isopropyl alcohol (900 mL) was added 4M hydrochloric acid solution in isopropyl alcohol (1.56 mL, 6.25 mol). The reaction mixture was heated to reflux temperature for 10 hours to 12 hours. The reaction mixture was cooled to 25° C. The reaction mixture was further stirred at 25° C. to 30° C. for 30 minutes, then the solid was filtered. The wet solid was washed with isopropyl alcohol (180 mL×2), and then dried under vacuum at 45° C. to 50° C. for 12 hours to afford the hydrochloride salt of 5-({4-[(2,3-dimethyl-2I-I- indazol-6-yl)(methyl) amino] pyrimidin-2-yl} amino-Z-methylbenzene sulfonamide as a light brown solid.

Yield: 97% w/w

We claim:

1. A process for the preparation of pazopanib of Formula Ia or salts thereof

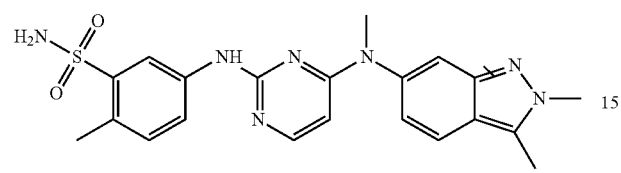
Formula Ia comprising:

i) treating 2,3-dimethyl-6-nitro-2H-indazole with Raney nickel to obtain a compound of Formula II;

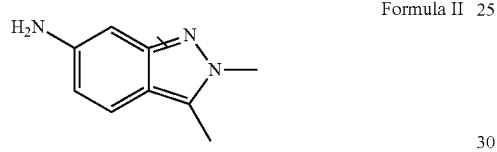
Formula II ii) treating the compound of Formula II at a temperature of 25° C. to 30° C. with 2,4-dichloropyrimidine to obtain a compound of Formula III

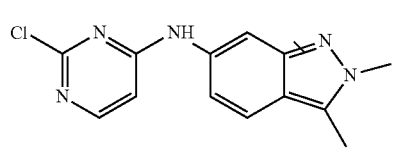
Formula III wherein steps i) and ii) are carried out in a single solvent comprising methanol circumventing heating and cooling procedures, and without isolating the compound of Formula II from the reaction mixture;

iii) converting the compound of Formula III to pazopanib of Formula Ia or salts thereof; and iv) isolating pazopanib of Formula Ia or salts thereof.

2. The process according to claim 1, wherein the treatment of the compound of Formula II with 2,4-dichloropyrimidine is carried out in the presence of a base.

3. The process according to claim 2, wherein the base is selected from the group consisting of an organic base and an inorganic base.

4. The process according to claim 3, wherein the organic base is selected from the group consisting of N,N-diisopropylethylamine, triethylamine, tri-isopropylamine, N,N-2-trimethyl-2-propanamine, N-methylmorpholine, 4-dimethylaminopyridine, 2,6-di-tert-butyl-4-dimethylaminopyridine, 1,4-diazabicyclo[2.2.2]octane, and 1,8-diazabicyclo[5.4.0]undec-7-ene, or mixtures thereof.

5. The process according to claim 3, wherein the inorganic base is selected from the group consisting of sodium carbonate, and potassium carbonate, sodium hydride, sodium bicarbonate, and potassium bicarbonate, or mixtures thereof.

6. The process according to claim 5, wherein the base is sodium bicarbonate.

* * * * *